Figure 1:
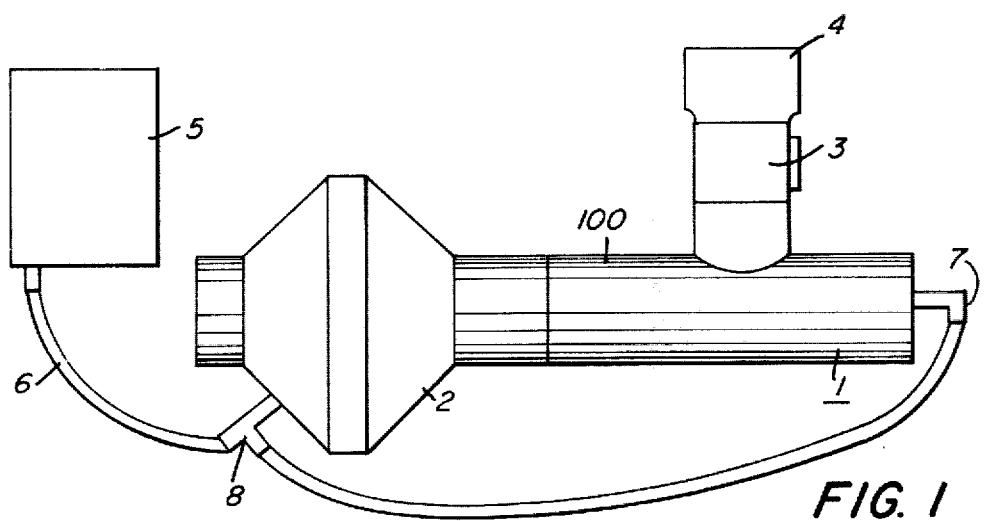
Figure 2:
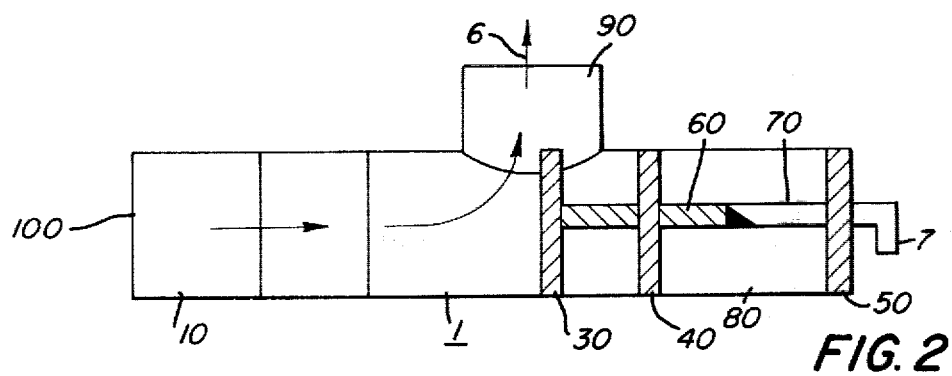
Figure 3:
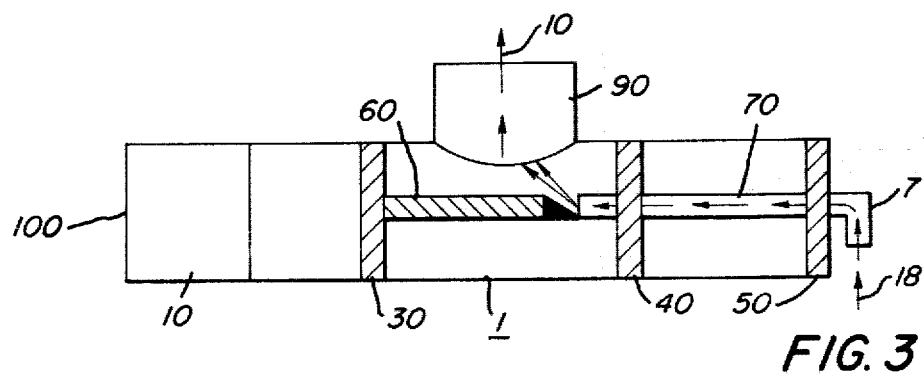

United States Patent [19]

Hallsey

[11] 4,331,140
[45] May 25, 1982

[54] SHUTTLE VALVE

[76] Inventor: Brian Hallsey, Apt. 4, River House, Penobscot Sq., Brewer, Me. 04412

[21] Appl. No.: 61,676

[22] Filed: Jul. 30, 1979

[51] Int. Cl.³ .......................................... A61M 16/00
[52] U.S. Cl. ........................... 128/204.26; 137/102; 137/DIG. 9; 128/204.25; 128/205.24
[58] Field of Search .............. 128/204.26, 204.25, 128/205.13, 205.24, 207.12, 200.18, 200.21; 137/112, DIG. 9

[56] References Cited

U.S. PATENT DOCUMENTS 3,630,196  12/1971  Bird et al. ............... 128/200.18
3,769,973  11/1973  Esbenshade, Jr. ........ 128/204.25 X

FOREIGN PATENT DOCUMENTS 1310608  10/1962  France ...................... 137/DIG. 9

Primary Examiner—Henry J. Recla
Attorney, Agent, or Firm—David F. Gould

[57] ABSTRACT

A shuttle type needle valve in a 'T' shaped body. The needle has a beveled end and a piston which co-operate with a central tube to permit fluid flow selectively from either of the two opposite arms of the 'T' shaped body to the central arm of the 'T' shaped body.

3 Claims, 3 Drawing Figures

U.S. Patent     May 25, 1982     4,331,140

SHUTTLE VALVE

BACKGROUND

1. Field of the Invention

My invention relates to fluid valves and more particularly relates to a needle valve of the shuttle type. The principle of the invention is a movable needle and associated piston which permit fluid flow selectively from either of the two opposite arms of a 'T' shaped body. This valve is useful in breathing apparatus where it is desired to supply a patient with measured medication in aerosol or vapor form along with air or oxygen.

2. The Prior Art

The prior art includes U.S. Pat. No. 2,445,505, to Ashton and U.S. Pat. No. 3,049,148 to Richardson. Both of these patents disclose two position shuttle valves. Valves of this type are designed to operate on a differential pressure basis.

In the field of respiratory medicine intermittent positive pressure breathing apparatus has been designed to deliver medication to a patient. A device called a nebulizer is available to deliver medication without interferring with the patient's natural pattern of breathing. However, the nebulizers of the prior art require the patient to manually actuate the medication source in synchronism with the patient's breathing. The medicine cannot be supplied on a continuous basis because it would be lost into the room when the patient was not inhaling from the apparatus. This would mean that there would be no control or record of the quantity of medication received by the patient. Also, valuable medication would be wasted. In particular, the prior art requires this to be a thumb actuated switch to control the dispensing of medication. The disadvantage of this system is that it does not work with patients who have their arms or hands immobilized or patients with poor coordination or other difficulties.

SUMMARY OF THE INVENTION

My invention is a solution to the problem of how to deliver medicine in vapor or aerosol form to a patient in synchronism with the patient's breathing. A 'T' shaped body having three hollow communicating arms is provided with a central tube mounted co-axially in one arm of the two opposite arms of the 'T' shaped body. A bevel ended needle is slidably mounted inside the central tube. The needle is mounted in a piston which can move freely between the two opposite arms of the 'T' shaped body. The position of the needle and piston determines whether the fluid shall flow from one opposite arm or the other of the 'T' shaped body to the central arm of the 'T' shaped body. In one position the piston blocks the central tube. In the other position of the piston, the piston blocks off one of the opposite arms of the 'T' shaped body. In this position, the beveled end of the needle permits fluid flow from the central tube. The needle is now almost out of the central tube but the dimensions of the needle and 'T' shaped valve body are chosen to keep the tip of the needle aligned with the tube while permitting fluid flow by the beveled end of the needle. As an alternative to the bevel on the end of the needle, other means may be used to permit fluid flow out of the central tube while keeping the needle aligned with the tube. For example, the right-hand end of the needle can be made hollow and be provided with ports to let fluid from the hollow end of the needle to the central arm of the 'T' shaped body.

DESCRIPTION OF DRAWINGS

FIG. 1 is an elevational view of the invention showing it associated with medication dispensing apparatus.

FIG. 2 is a longitudinal sectional view of the invention showing the piston sealing the central tube with fluid flow from the left.

FIG. 3 is a longitudinal sectional view of the invention with the piston in the position of maximum needle withdrawal from the central tube with fluid flow from the right.

DESCRIPTION OF PREFERRED EMBODIMENT

As shown in the drawings, where like numerals refer to like parts throughout, a 'T' shaped body 1 is provided with two opposite hollow arms 80 and 100. In communication with both of these arms is a central hollow arm 90. A central tube 70 is mounted coaxially with the arm 80. The central tube 70 may be mounted in the center of the arm 80 by means of a fluid tight plug 50. An additional support 40 may be provided for the central tube 70 if it is necessary. A bevel ended needle 60 is slidably positioned in the central tube 70. On the end of the needle 60 remote from the beveled end is mounted a slidable piston 30. As will be described later, this piston 30 serves selectively to seal the interior end of central tube 70 and the hollow arm 100 of the 'T' shaped body 1. Therefore it is important that both sides of the piston 30 have sealing means such as gaskets. Alternatively, the piston 30 itself may be made of a sealing material such as plastic.

Referring to FIG. 1 it may be seen that the valve 1 of the invention may be incorporated with a medication dispenser such as the nebulizer 2. The nebulizer 2 is connected to arm 100 of the invention. A mouth piece 4 is connected to the hollow central arm 90 of the invention. The central tube 70 is connected by means of a hose 7 to a small tee 8 on the far end of the nebulizer 2. A hose 6 connects the nebulizer 2 through tee 8 to a source of oxygen or compressed air such as tank 5. The tee 8 is also connected to the exterior end of the central tube 70.

OPERATION

In operation, the patient would be breathing through the mouth piece 4 of FIG. 1. The mouth piece 4 is connected to a one way exhalation valve 3. The medication would be placed in the nebulizer 2. The patient would normally be breathing air or oxygen from the tank 5 through the hose 6. The flow of air through the hose 7 would be blocked by the valve of the invention 1 as shown in FIG. 2. At this time, the air or oxygen would enter the nebulizer 2 where it would pick up medication and deliver it to the arm 100 of the valve 1. From there the medicated air would flow through the central arm 90 and the exhalation valve 3 to the mouth piece 4. It will be observed from FIG. 1 that the air or oxygen tank 5 is connected to the hollow arm 100 of the valve by means of hose 6 through tee 8 and the nebulizer 2. The tee 8 also bypasses a portion of the breathing air or oxygen through hose 7 to the central tube 70.

First the 'off' or no medication supplied position of the valve 1 will be explained. The air or oxygen pressure in hose 7 pushes the needle 60 almost all the way out of the central tube 70 by means of the piston 30. This may be best seen in FIG. 3. Inertia carries the needle 60 after the beveled end lets fluid escape. In this position, the air or oxygen pressure presses against the right hand side of the piston 30 and closes off the hollow arm 100. This cuts off the nebulizer 2 and no medication goes through the valve 1 to the mouth piece 4. It will be noted that in this 'off' position air or oxygen pressure is simultaneously being supplied to the nebulizer 2 by means of the tee 8. However, the nebulizer 2 is a high resistance path because it contains a very small atomizer port. This means that very little air pressure gets through the nebulizer 2 to the left hand side of piston 30. The pressure on the right hand side of the piston 30 is much greater because it is coming from a low resistance path through hose 7 and central tube 70. This keeps hollow arm 100 sealed and no medication escapes through valve 1.

Now the 'on' position of the valve 1 will be described with reference to FIGS. 1 and 2. This is the position in which the patient receives medication from the nebulizer 2 through the mouth piece 4. When the patient inhales through the mouth piece 4, the negative pressure of his inhalation is enough to overcome the air or oxygen pressure from central tube 7 against the right hand side of the piston 30. The piston 30 is then moved to the right to the position shown in FIG. 2. In this position the piston 30 seals the central tube 70. The movement of the piston 30 to the right is helped by the small flow of air or oxygen through the high resistance nebulizer 2. A path is thus established from the nebulizer 2 through the hollow arm 100 and the common arm 90 of the 'T' shaped valve to the mouth piece 4. The air or oxygen pressure through hose 7 is not great enough to force the piston 30 away from its sealing relation with the central tube 70. When the patient stops inhaling, the loss of negative pressure in central arm 90 gives the air or oxygen pressure in central tube 70 the opportunity to push the piston 30 all the way to the left. This again stops the flow of medication from the nebulizer 2. It is important to note that the area of the piston 30 in contact with the central tube 70 is much smaller than the area of the piston 30 that is exposed to the negative pressure of the patient's inhalations. This makes it easier for the patient to turn the valve to the on or medication supplied position shown in FIG. 2.

My invention conserves medication when the patient is not inhaling and enables an inhalation therapist to accurately measure how much medication the patient has inhaled from the nebulizer 2.

The foregoing is considered as illustrative only of the principles of the invention. Furthermore, some numerous modifications and changes will readily occur to those skilled in the art, it is not desired to limit the invention to the exact construction and operation shown and described, and accordingly all suitable modifications and equivalents may be resorted to falling within the scope of the invention as claimed.

I claim:

1. A shuttle type needle valve comprising a three armed body having first and second opposite hollow arms and a central hollow arm all in communication with each other, said central hollow arm including means adapted to be connected to the breathing passages of a patient, a tube adapted to be connected to a source of pressurized gas mounted coaxially in the first of the opposite hollow arms, the first of said opposite hollow arms having at least one plug in the end remote from said central arm, said tube mounted through the plug in the first of said opposite hollow arms to permit passage of gas through said plug, the second of said opposite hollow arms having an opening at the end remote from said central arm and adapted to be connected to a source of breathing gas, needle means slidable mounted in said tube, piston means connected to said needle means, said needle and piston means slidable toward the first hollow arm to seal said tube when suction is applied to the central arm, gas pressure from the tube urging said needle and piston means toward the second hollow arm to seal said second hollow arm when the suction stops in the central arm.

2. The shuttle type needle valve of claim 1 in which the needle is provided with means to permit fluid flow from the tube while maintaining needle alignment with the tube.

3. The shuttle type needle valve of claim 2 in which the means to permit fluid flow from the tube while maintaining needle alignment with the tube is a bevel on the end of the needle that slides in the tube.

* * * * *